US00PP34649P2

(12) United States Plant Patent
Elsworth

(10) Patent No.: US PP34,649 P2
(45) Date of Patent: Oct. 11, 2022

(54) ***AJUGA* PLANT NAMED 'PARPAR'**

(50) Latin Name: *Ajuga reptans*
Varietal Denomination: 'Parpar'

(71) Applicant: Kelly Elsworth, Portage, MI (US)

(72) Inventor: Kelly Elsworth, Portage, MI (US)

(73) Assignee: Christopher M. Hansen, Zeeland, MI (US)

( * ) Notice: Subject to any disclaimer, the term of this patent is extended or adjusted under 35 U.S.C. 154(b) by 0 days.

(21) Appl. No.: 17/687,371

(22) Filed: Mar. 4, 2022

(30) Foreign Application Priority Data

Dec. 23, 2021 (QZ) ..... 20213445

(51) Int. Cl.
*A01H 6/00* (2018.01)
*A01H 5/02* (2018.01)

(52) U.S. Cl.
USPC ..... Plt./401

(58) Field of Classification Search
USPC ..... Plt./401
CPC ..... A01H 6/00; A01H 5/02
See application file for complete search history.

*Primary Examiner* — Keith O. Robinson
(74) *Attorney, Agent, or Firm* — Penny J. Aguirre

(57) ABSTRACT

A new cultivar of *Ajuga* plant named 'Parpar' that is characterized by its foliage that emerges dark burgundy in color and matures to yellow-green with apricot-burgundy colors as they mature; creating multi-colored foliage that exists at the same time, its foliage that is vibrant red in winter, and its high resistance to sun scorch and thrives in full sun in the summer in Michigan.

2 Drawing Sheets

Botanical classification: *Ajuga reptans.*
Variety denomination: 'Parpar'.

CROSS-REFERENCE TO RELATED APPLICATIONS

This application claims priority to European Community Plant Variety Office (CPVO) Plant Breeder's Rights Application No. 2021/3445 filed on Dec. 23, 2021, under 35 U.S.C. 119(f), the entire contents of which is incorporated by reference herein. This application is also co-pending with a U.S. Plant Patent Applications filed for a plant derived from the same breeding program that is entitled *Ajuga* Plant Named 'Trotou' (U.S. Plant patent application Ser. No. 17/687,440).

BACKGROUND OF THE INVENTION

The present invention relates to a new and distinct cultivar of *Ajuga reptans* and will be referred to hereafter by its cultivar name, 'Parpar'. 'Parpar' represents a new cultivar of *Ajuga*, an herbaceous perennial grown for landscape use.

The new Invention arose from an ongoing controlled breeding program in Hudsonville, Mich. The objective of the breeding program is to develop new cultivars of *Ajugas* with unique foliage coloration, different leaf sizes and strong clump forming growth habits.

The new cultivar arose from a controlled cross made by the Inventor in March of 2019 between an unnamed and unpatented plant of *Ajuga reptans* with gold foliage as the female parent and 'Black Scallop' (U.S. Plant Pat. No. 15,815). The Inventor selected 'Parpar' as a single unique plant from amongst the seedlings of the above cross in May of 2020.

Asexual propagation of the new cultivar was first accomplished by stem tip cuttings in June of 2020 in Hudsonville, Mich. Propagation by stem tip cuttings and division has determined the characteristics to be stable and reproduced true to type in successive generations.

SUMMARY OF THE INVENTION

The following traits have been repeatedly observed and are determined to be the characteristics of the new cultivar. These attributes in combination distinguish 'Parpar' as a unique cultivar of *Ajuga.*

1. 'Parpar' exhibits foliage that emerges dark burgundy in color and matures to yellow-green with apricot-burgundy colors as they mature; creating multi-colored foliage that exists at the same time.
2. 'Parpar' exhibits foliage that is vibrant red in winter.
3. 'Parpar' exhibits a high resistance to sun scorch and thrives in full sun in the summer in Michigan.

The female parent plant of 'Parpar' differs from 'Parpar' in having foliage that is all yellow in color that turns brown in winter and flowers that are pink in color. The male parent plant of 'Parpar' differs from 'Parpar' in having foliage that is purple in color during the growing season and in winter. 'Parpar' can be most closely compared to *Ajuga reptans* cultivars 'Gold Chang' (U.S. Plant Pat. No. 32,751) and 'Trotou'. 'Gold Chang' is similar to 'Parpar' in having foliage that is gold in color and a hardy groundcover growth habit. 'Gold Chang' differs from 'Parpar' in having flowers that are light pink in color, foliage that is all gold in color, stems that are lime green in color, and in being highly susceptible to sun scorch. 'Troutou' is similar to 'Parpar' in having flowers that are blue in color, yellow colored foliage, and a hardy groundcover growth habit. 'Troutou' differs from 'Parpar' in having foliage that all yellow in color and turn dark tan in winter.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but are not limited to website publications by Romence Gardens, Spring Hill Nursery, Growing Colors, Garden Solutions Plants, Sugar Creek Gardens, Great Garden Plants, Pahls, Winter Green House, Plant Delights, Gateway Gardens, In the Country Garden and Gifts, White House Perennials, Etsy, Mountain Crest Gardens, Peace Tree Farm, Campbells Nursery, Houzz, Floral Acres, Quality Cuttings, Honeymoon Acres, Pinterest, Blue Sky Nursery, Groffs Plant Farm, Plant Central, jlbg blog, Phoenix Perennials, Creedside Gardens Inc, Timber Pine Store, Landscape Hub, Facebook, The Greenery, Carp Garden Centre, George Weigel, Fine Gardening, Chicago Botanic, Rideau Woodland Ramble, Preen, Hennepin Tech, YouTube, jcra.ncsu, Pleasant Run Nursery, Green Profit, Instagram, BHG, Earth, Sunset Nursery, Dianes Greenhouse, Luxury Mantels, Online Flipping Book, Bill Moore Co, Betoncilasi, Coleman Nursery, SVG Plants. Calemeo, Eason Horticultural Resources, Mays Greenhouse, Michell's, Zyromski, Masboni, Plant Lust, Penn Live, BFG Supply, Park Stone, and Masty Young Plants.

BRIEF DESCRIPTION OF THE DRAWINGS

The accompanying color photographs illustrate the overall appearance and distinct characteristics of the new *Ajuga* as grown in a greenhouse in Hudsonville, Mich.

The photograph in FIG. 1 provides a view of a 2-year-old plant of 'Parpar' starting to bloom as grown in a 1-gallon container.

Figure 1:
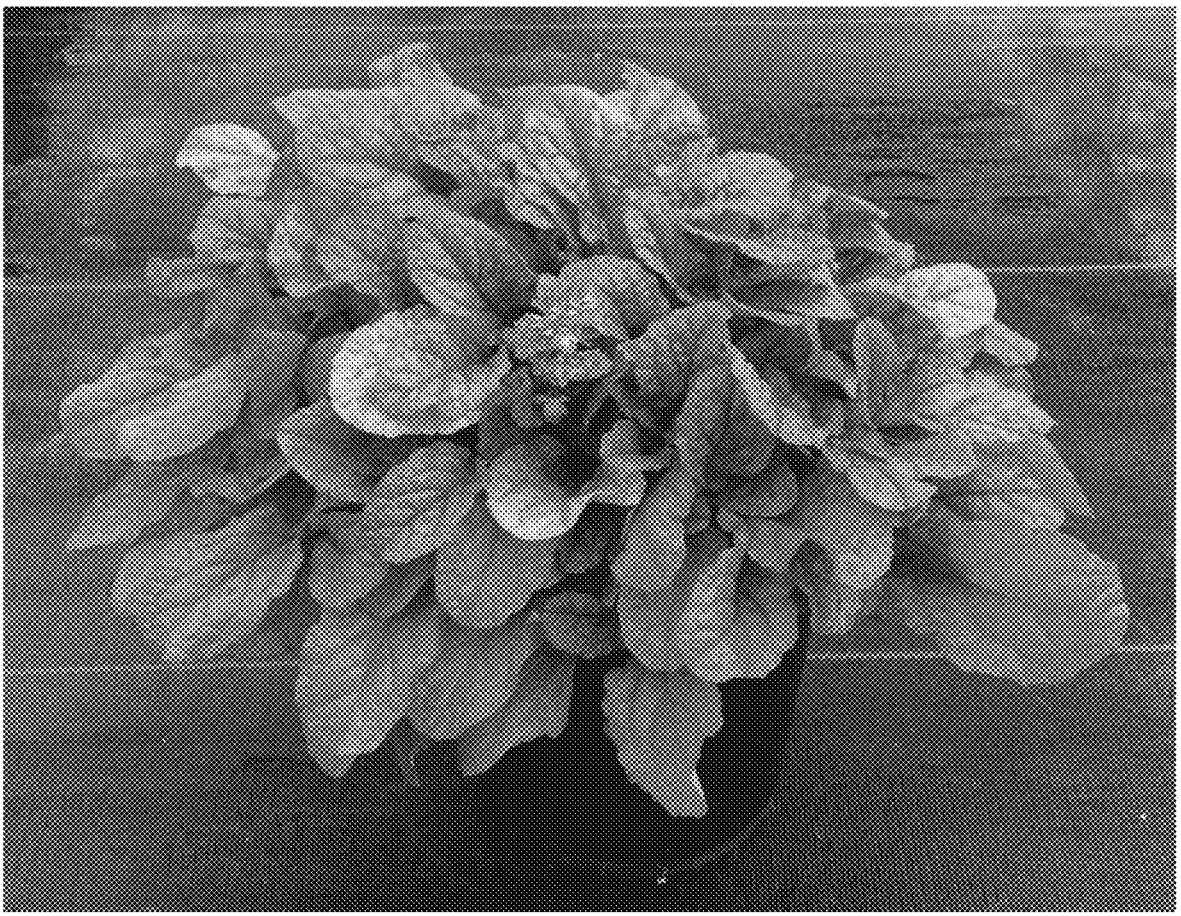
Figure 2:
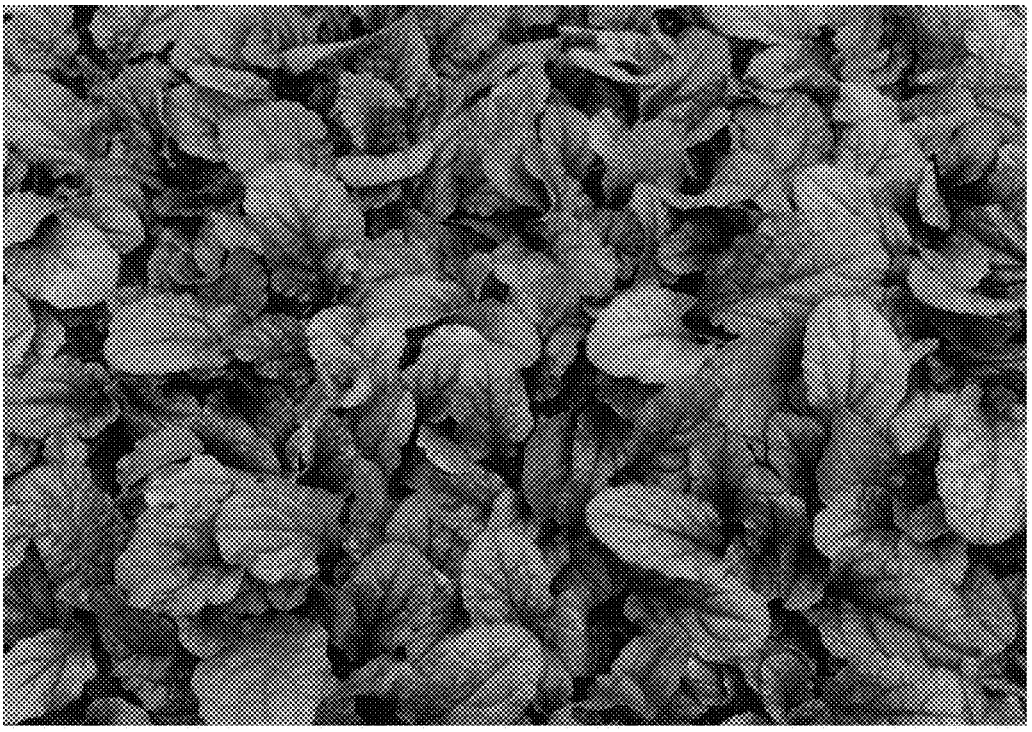

The photograph in FIG. 2 provides a close-up view of the foliage of a 2-year-old plant of 'Parpar' as grown in a 1-gallon container.

Figure 3:
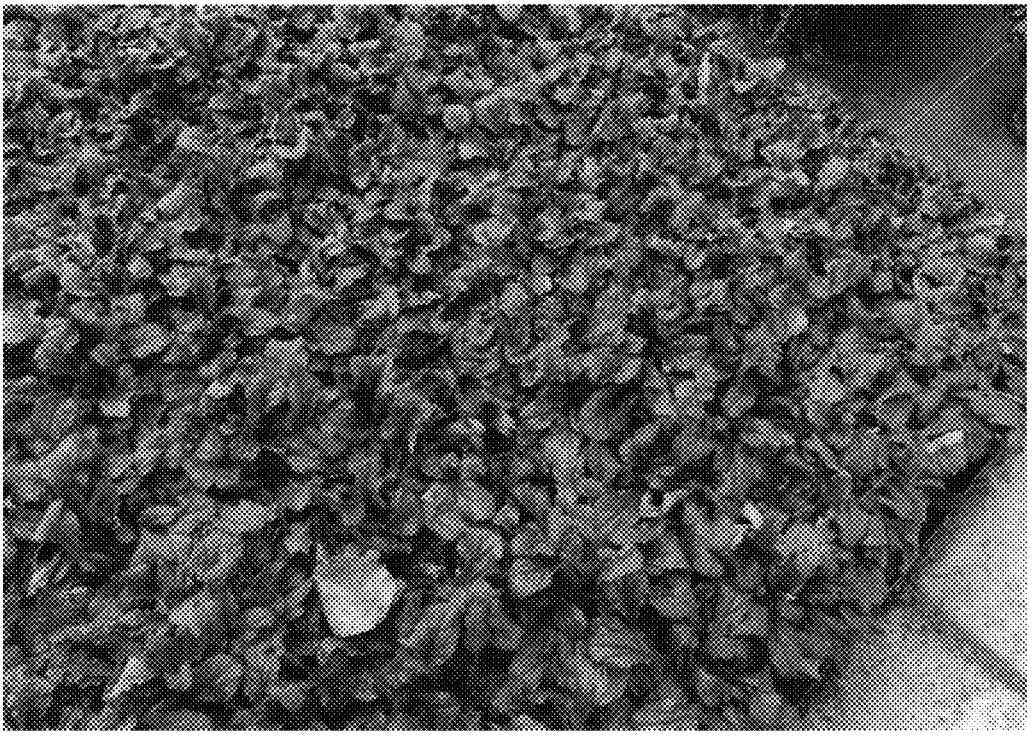

The photograph in FIG. 3 provides a top view of the winter foliage of 6-month-old plants of 'Parpar' as grown in 50-cell plugs.

The colors in the photograph may differ slightly from the color values cited in the detailed botanical description, which accurately describe the colors of the new *Ajuga*.

DETAILED BOTANICAL DESCRIPTION

The following is a detailed description of 6-month-old plants of the new *Ajuga* as grown in 4-inch containers in a greenhouse in Hudsonville, Mich. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

Blooming period: 14 to 6 weeks in late spring into summer in Michigan.

Plant type: Herbaceous perennial.

Plant habit: Dense, groundcover, compact upright inflorescences.

Height and spread: 11 cm in height (soil level to top of floral plane), an average of 7.5 cm in height (soil level to top of foliar plane) and 17 cm in width, a mature plant in the landscape reaches an average of 10 cm in height and 46 cm in spread.

Hardiness: At least in U.S.D.A. Zones 4 to 8.

Diseases and pests: Plants have been observed to be disease free, however no resistance to any specific diseases is known, no resistance or susceptibility to pests has been observed.

Root description: Fine and fibrous, a blend of 158A and NN155A in color.

Propagation type: Stem cuttings and division.

Root development: An unrooted stem cutting will fully root in a 50-cell plug in 8 weeks and a 50-cell plug will fully root in a 1-gallon container in 10 weeks.

Growth rate: Vigorous.

Branching habit: Basal rosettes of leaves from rhizomes.

Foliage description:

*Leaf shape*.—Spatulate.

*Leaf division*.—Simple.

*Leaf base*.—Truncate to base of rhizome.

*Leaf apex*.—Broadly acute to rounded, sometimes notched.

*Leaf venation*.—Pinnate, matches surface colors.

*Leaf margins*.—Moderately undulate.

*Leaf attachment and arrangement*.—Whorled, held in in clumps.

*Leaf orientation*.—Emerge upright and then outward and bending downwards.

*Leaf surface*.—Very finely puberulent on upper surface, slightly rough to the touch, glossy, lower surface glabrous and glossy, base of leaves covered with long woolly pubescence up to 3 mm in length and NN155D in color.

*Leaf color*.—Young and mature upper surface; 138A, becoming flushed with 175A and 187A, and then fully changing to 187A as the leaf ages, base 184C, young and mature lower surface; 148B, main vein and base of leaf becomes very lightly flushed with a blend of 184C as the leaf ages, peduncle leaves; upper and lower surface base 92D, center, margins and top 187B and 184A, winter upper and lower surfaces; a blend of 70A and 187A.

*Leaf size*.—Average of 9 cm in length, 3 cm in width.

*Leaf quantity*.—Average of 30 in a clump 4 cm in diameter.

*Leaf attachment*.—Sessile.

Flower description:

*Inflorescence type*.—Verticillaster, terminal spike, individual flowers in clusters held in leaf-axils.

*Inflorescence size*.—An average of 7 cm in height and 4 cm in width.

*Inflorescence number*.—An average of 45 as a fully mature plant grown in a 1-gallon container.

*Lastingness of inflorescence*.—10 to 14 days, self-cleaning.

*Flower type*.—Labiate.

*Flower number*.—Average of 35 per inflorescence.

*Flower fragrance*.—None.

*Flower buds*.—Oblanceolate in shape, average of 3 mm in length and 2 mm in diameter, color; smaller immature buds 150D, larger maturing buds 91A to 91B, immature calyx 91A to 91B, surface matte and densely covered with long, soft woolly pubescence up to 3 mm in length and matching surface colors.

*Flower size*.—Average of 1.3 cm in depth, 1 cm in diameter, throat 2.5 mm in diameter, tube 8 mm in length and 2 mm in diameter.

*Peduncles*.—An average of 4.5 cm in length, 3 mm in diameter, vertical angle, moderately strong, color; 145D, surface is very densely covered with long woolly hairs; up to 3 mm in length, translucent and matching surface color.

*Calyx*.—Rotate and tubular in shape, 2 mm in length and diameter.

*Sepals*.—5, 55% fused at base, average of 2 mm in length, 1 mm in width, ovate in shape, apex acute, entire margins, surface is heavily covered with long woolly hairs 92B and NN155D in color and translucent, color; inner and outer surface 91B and 91D, tips 145A.

*Petals*.—55% of petals fused into tube, upper central lobe; notched, average of 7 mm in length, 7 mm in width, rounded in shape, obtuse apex, entire margins with no undulation, upper and lower surface glabrous, satiny, color; upper surface when opening and fully open N89C, edges N89A, striped in center 91C, lower surface when opening and fully open 92A and 92B, outer lobes; 2, average of 5 mm in length, 3 mm in width, oblanceolate in shape, apex is obtuse, entire margins, no undulation, upper and lower surface glabrous and velvety, color; N89C, edges N89A, lower surface when opening and fully open 92A and 92B, flower throat and tube; outer surface covered with woolly soft pubescence, inner surface is smooth and glabrous, color; inner and outer surface when opening and fully open 92B.

Reproductive organs:

*Pistils*.—1, style; 6 mm in length, 91C in color, stigma; non-distinguishable, ovary; oblong, 2 mm in length, 1 mm in width, NN155D in color.

*Stamens*.—5, filament; implanted into flower tube, average of 5 mm in length, top N89A, mid-section to base 91C in color, anthers; club-shaped, 0.5 mm in diameter, 203A in color, pollen; moderate in quantity, 23B in color.

*Fruit*.—Fruit and seed production has not been observed to date.

It is claimed:

1. A new and distinct variety of *Ajuga* plant named 'Parpar' as described and illustrated herein.

* * * * *